United States Patent

Gagliano

[11] Patent Number: 5,634,514
[45] Date of Patent: Jun. 3, 1997

[54] KILN FOR FIRING AND OR CASTING PROSTHODONTIC PRODUCTS

[75] Inventor: Alberto Gagliano, Cavalcaselle Di Castelnuovo Del Garda, Italy

[73] Assignee: Peacock Limited L.C., Cheyenne, Wyo.

[21] Appl. No.: 567,597

[22] Filed: Dec. 5, 1995

Related U.S. Application Data

[62] Division of Ser. No. 305,277, Sep. 13, 1994, Pat. No. 5,496,017.

[30] Foreign Application Priority Data

Sep. 20, 1993 [IT] Italy .................. VR93A0069
Sep. 28, 1993 [IT] Italy .................. VR93A0072

[51] Int. Cl.⁶ .................. B22D 27/13; B22D 27/15
[52] U.S. Cl. .................. 164/495; 266/44; 266/208; 222/590; 164/68.1; 164/136
[58] Field of Search .................. 266/208, 207, 266/250, 44; 432/11, 13, 128, 198; 222/590, 591; 164/7.1, 136, 48, 492, 493, 61, 65, 68.1, 495

[56] References Cited

U.S. PATENT DOCUMENTS

| | | | |
|---|---|---|---|
| 3,336,971 | 8/1967 | Tingquist et al. | 266/208 |
| 3,510,546 | 5/1970 | Wentzell | 266/208 |
| 3,747,808 | 7/1973 | Richman | 164/136 |
| 3,952,408 | 4/1976 | Docx | 29/611 |
| 4,300,037 | 11/1981 | Padden | 219/492 |
| 4,498,866 | 2/1985 | Meislitzer et al. | 266/208 |
| 4,653,732 | 3/1987 | Wunning et al. | 266/250 |
| 4,917,359 | 4/1990 | Ichikawa et al. | 266/208 |

FOREIGN PATENT DOCUMENTS

| | | |
|---|---|---|
| 0018450 | 11/1980 | European Pat. Off. |
| 0087111 | 8/1983 | European Pat. Off. |
| 0091742 | 10/1983 | European Pat. Off. |

*Primary Examiner*—Scott Kastler
*Attorney, Agent, or Firm*—Greer, Burns & Crain, Ltd.

[57] ABSTRACT

The firing and/or casting kiln has a containment casing which internally forms a treatment chamber, a part holder which is movably mounted inside the treatment chamber, an opening for access to the treatment chamber, and a conditioning system for producing a vacuum and introducing inert gas into the treatment chamber.

4 Claims, 2 Drawing Sheets

KILN FOR FIRING AND OR CASTING PROSTHODONTIC PRODUCTS

This is a division, of application Ser. No. 08/305,277, filed Sep. 13, 1994, now U.S. Pat. No. 5,496,017.

BACKGROUND OF THE INVENTION

The present invention relates to a kiln for firing or casting prosthodontic products.

In the manufacture of dental prostheses, false teeth made of ceramic material, supported on a core or support constituted by a titanium casting, are becoming increasingly widespread. The stable coupling between the ceramic material and the titanium support is achieved by firing the ceramic material on the metal support. In order to avoid the formation of oxides on the surface of the metal support, which would compromise the metallic structure and thus the adhesion and anchorage of the ceramic material, firing must occur in an inert atmosphere.

The kilns that have been used so far allow firing in an inert atmosphere, but the operator, after removing the part from the muffle, must wait for a long time (a few hours) before he can continue with the necessary work for finishing the prosthesis, since it is necessary to wait for the complete cooling of the prosthesis in the closed kiln; the productivity of a firing operation is therefore very low.

Italian patent application VR93A000012, filed Feb. 18, 1993 in the name of the same Applicant, discloses a process and an apparatus for casting in an inert atmosphere which uses a crucible placed adjacent to a casting cylinder which contains refractory material with an impression: the crucible and the cylinder are located within a sealed casting chamber. The casting chamber can be tilted to cast the molten metal into the crucible by gravity. The ambient air contained by the crucible section and by the cylinder section is aspirated by means of a pneumatic circuit connected to a vacuum pump. After producing a certain degree of vacuum, the aspiration circuit is disconnected and inert gas is introduced from the crucible section; said gas passes through the chamber that contains the crucible and the casting chamber and the related impressions, performing an effective flushing action. After casting, inert gas at a relatively high pressure is introduced in the chamber that contains the crucible in order to inject, by pressure, the molten metal into the casting cylinder; the aspiration circuit is then disconnected from the casting chamber section as well, the unit is opened and the casting cylinder is removed from the muffle.

Such a solution according to the above mentioned patent application, while being a considerable improvement over the prior state of the art, is in practice affected by some limitations that sometimes negatively affect the quality of the products, which is not always uniform. First of all, lack of control over pressure, which does not remain constant during casting, can cause non-uniform castings and defects in the form of bubbles or porosities. The continuous operation of the aspiration circuit in the casting cylinder section can cause a relatively high pressure difference and thus increase the casting speed, inducing vortical motions in the liquid and thus bubbles inside the cast. Furthermore, the refractory material that constitutes the impression is porous and thus tends to absorb and retain oxygen particles even after vacuum has been produced, releasing them later during casting, thereby reducing the quality of the cast.

SUMMARY OF THE INVENTION

A principal aim of the present invention is to provide a firing or casting kiln which ensures high operating efficiency without producing rejects or breakages on the processed products.

A specific object of the present invention is to provide a kiln or firing and cooling device for ceramic material mounted on a metal support that allows to perform both firing and subsequent cooling in a controlled atmosphere in a very short time.

Another object of the present invention is to provide a firing and cooling kiln which features automated operation, is highly reliable, and has a low manufacturing cost.

Another specific object of the present invention is to provide a kiln for inert-atmosphere casting that allows to obtain prosthodontic products of good quality and with a practically finished outer surface; this also makes any subsequent work for finishing said products faster and therefore cheaper.

According to a first aspect of the present invention, a firing and/or casting kiln is provided which comprises:

a containment casing which internally forms at least one treatment chamber;

at least one part holder which is movably mounted inside the, or the at least one, respective treatment chamber;

at least one opening for access to the or each treatment chamber; and conditioning means for producing a vacuum and introducing inert gas in the or each treatment chamber.

According to another aspect of the present invention, a process for casting in inert atmosphere and at a controlled pressure one or more loads of titanium is provided which comprises, in sequence:

the preparation of a metal load to be cast in a crucible which is located adjacent to a casting cylinder with refractory material and an impression, said crucible and said cylinder being arranged within a sealed melting and casting chamber that can be tilted and has electric-arc melting means for the load, means for aspirating the air from the crucible section and from the cylinder section, at least one source for dispensing inert gas in the crucible section, and a discharge valve;

the provision, in a time interval of at least two minutes, of a vacuum of at least 4 millibar within the melting and casting chamber, said vacuum being controlled by a high-vacuum device by aspirating from the cylinder section in order to adequately degas the refractory material that delimits the casting impression;

the supply of inert gas at a low flow-rate, on the order of approximately 3–4 liters/minute, to "pre-flush" the casting chamber;

the activation of electric-arc means to melt the load;

the interruption of the aspiration;

the supply of inert gas until the melting and casting chamber is saturated;

the tilting of the casting chamber to cast from the crucible to the casting cylinder;

the supply of inert gas with a high flow-rate to push the molten metal so that it enters the material inside the casting cylinder;

the controlled discharge of the inert gas, from the casting cylinder section towards the outside, at a threshold value that is equal to, or slightly higher than, the external atmospheric pressure, so as to have quick casting at constant pressure;

and the removal of the casting cylinder from the casting chamber.

BRIEF DESCRIPTION OF THE DRAWINGS

Further characteristics and advantages of the present invention will become apparent from the following detailed description of two currently preferred embodiments of the firing and/or casting kiln, given only by way of non-limitative example with reference to the accompanying drawings, wherein.

DESCRIPTION OF THE PREFERRED EMBODIMENTS

Figure 1:
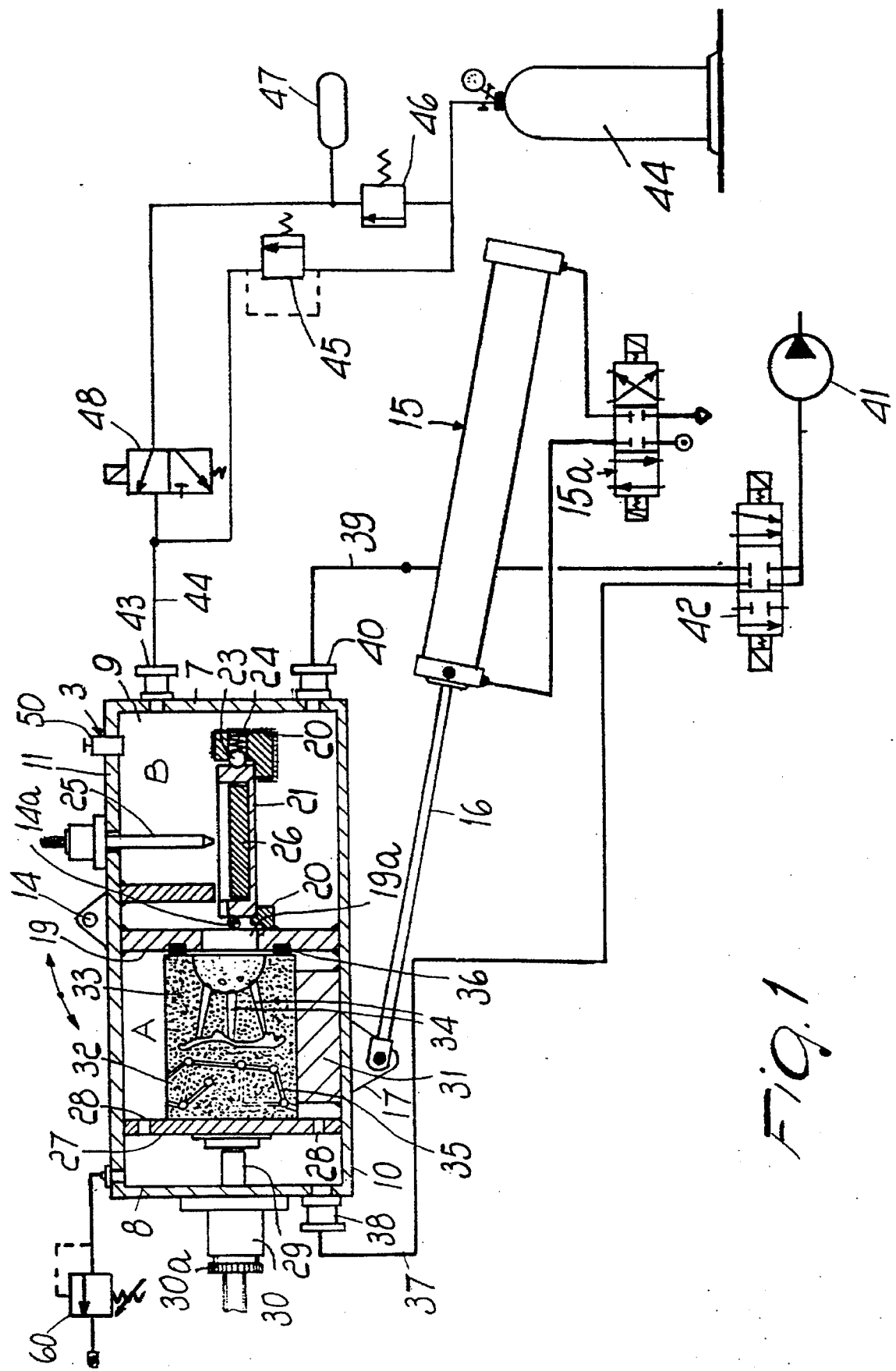
FIG. 1 is a schematic view of a tilting casting chamber with some parts shown in cross-section.

Initially with reference to FIG. 1, said figure illustrates a casting apparatus which includes a casting chamber 3 rotatably mounted about a horizontal axis, for example a pivot 14, so that the chamber 3 is rotatably supported. In order to tilt the chamber 3 about the axis of the pivot 14 there is, for example, a linear actuator which is constituted by a hydraulic or pneumatic cylinder-and-piston double-action unit 15 with a stem 16 that is articulated to a lug 17. The unit 15 is supplied by a suitable source of pressurized fluid by means of an electropneumatic control valve 15a.

The space of the chamber 3 is divided into two compartments A and B by an intermediate partition 19 with an opening 19a for connecting the compartments.

A crucible 21 is provided in the compartment B and can be seated on a bracket 20 at an electrode 25 that generates an electric arc for melting a metal pellet 26 placed in the crucible 21.

The compartment A contains a supporting pan 27 provided with holes 28 for the passage of the inert gas and of the air to be aspirated.

The compartment A has a safety valve or vent valve 60 of any suitable type which is arranged externally and meant to control the pressure of the inert gas so that it is kept equal to, or slightly higher than, atmospheric pressure throughout the casting, so as to avoid injecting inert gas in the molten metal and thus avoid forming bubbles and/or porosities.

With the above described apparatus, provided with a vent valve 60, first of all the casting cylinder 32 is loaded into the compartment A, moving the end of the casting cylinder that corresponds to the inlet of the casting so that it abuts against the annular gasket 36. Then a titanium pellet 26 is loaded into the crucible 21.

The pump 41 is then activated to produce a vacuum of approximately 4 millibar which is controlled by a Pirani-type probe. This operation continues for two or preferably three minutes, so as to ensure that the time is sufficient to degas the refractory 33. Then the duct 39 is closed by means of the electric valve 42, while aspiration from the compartment A continues through the duct 37 and simultaneously low-pressure argon is fed into the compartment B to "pre-flush" the entire casting chamber.

The inert gas in fact passes from the compartment B through the opening 19a of the partition 19 and, by virtue of the gasket 36, is forced to pass through all of the impression 34 and exit through the vent channels 35 before it is aspirated into the duct 37 through the holes 28 of the pan 27.

At this point the aspiration pump 41 is halted and a few seconds later the electrode 25 is energized to produce the electric arc and cause melting, generally within 45 seconds. During the melting of the titanium, the inert gas continues to enter the compartment B at a flow-rate of approximately 4 liters/minute and therefore the compartments A and B saturate with argon (in approximately 30 seconds).

The valve 15a is then energized, activating the double-action cylinder 15 which in turn tilts the casting chamber 3 through 90° so as to cast the metal.

At this point the check valve 48 is opened and injects into the compartment B, at a relatively modest pressure, inert gas that originates from the argon reserve 47; accordingly, a mild pressure-casting of the metal cast inside the impressions and the vent channels of the cylinder 32 occurs. However, most of the inert gas is discharged into the atmosphere by means of a safety valve 60 which thus keeps the pressure inside the casting chamber constant throughout the casting at a level that is equal to, or slightly higher than, approximately one atmosphere; this prevents the formation of defects and irregularities (bubbles, porosities) in the molten metal.

It is evident that the above described process allows to perform casting while the casting cylinder 32 is cold, with a controlled ambient pressure and in an inert atmosphere, so as to eliminate the risk that said cylinder might react with oxygen to form oxides and with nitrogen to produce nitrides that could compromise the quality of the cast. The cast thus has almost-finished surfaces which only require a quick sanding.

Figure 2:
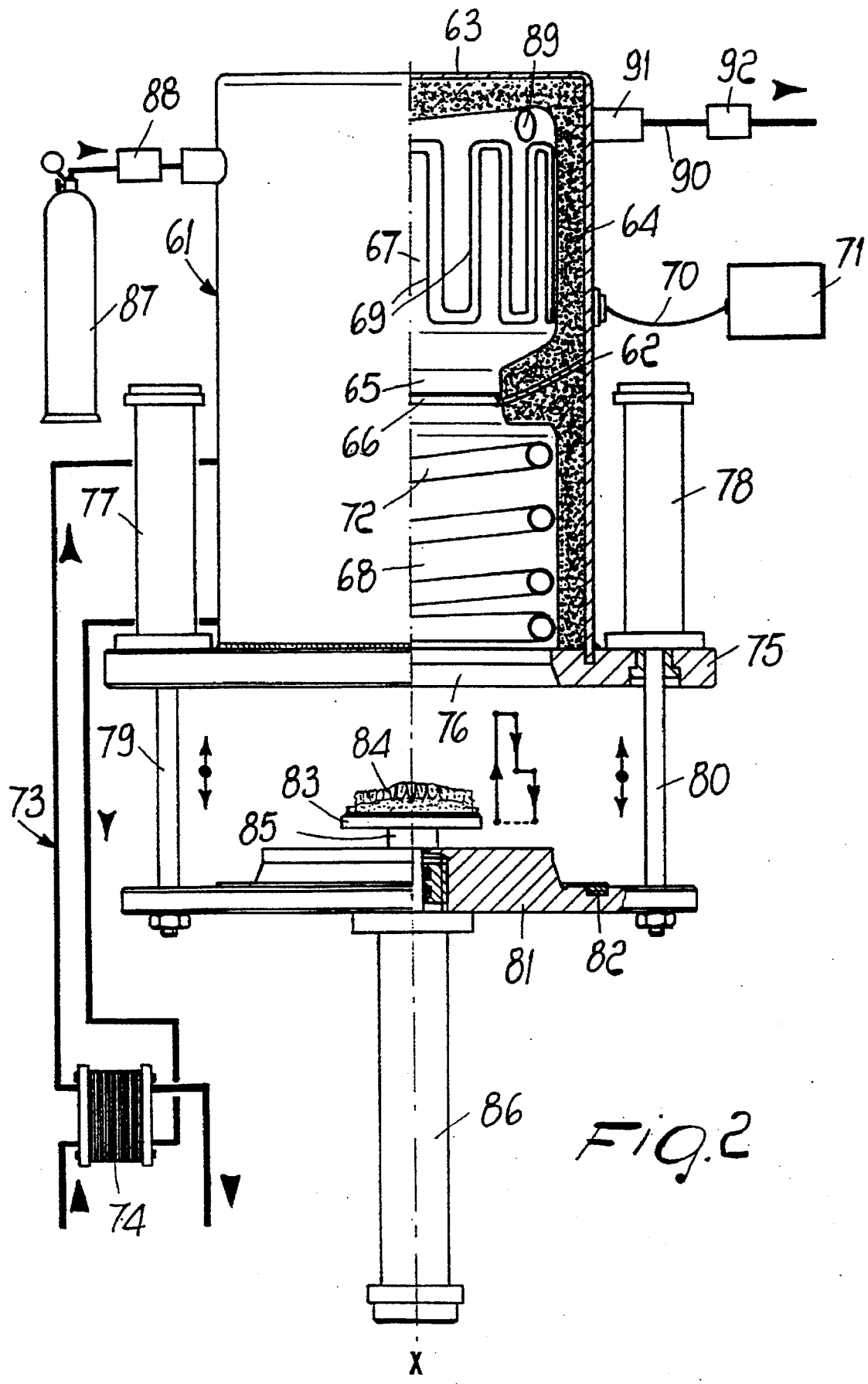
FIG. 2 is a partially sectional schematic view of a firing and cooling apparatus according to the present invention.

The embodiment shown in FIG. 2 illustrates a firing and cooling apparatus which is formed by a metal casing 61, made for example of stainless steel plate, with a cylindrical internal opening and with a side wall 62 and a closed bottom 63. The inside of the casing is lined with one or more layers of a suitable insulating material 64 which can be configured so as to have an intermediate flange-like portion 65, which optionally includes an annular core 66 made of stainless steel that is welded to the side wall 62; said flange-like portion delimits a kiln chamber or compartment 67 and a cooling compartment or chamber 68.

The kiln chamber 67 is provided with suitable heating means, for example coil-shaped electric resistors 69 which are electrically connected, by means of a cable 70, to a control unit 71 which is in turn supplied by a suitable source of electric power.

The cooling chamber 68 is instead surrounded by a metal coil 72 whose ends are connected to a circuit, generally designated by the reference numeral 73, for the forced circulation of a heat-transferring liquid, for example water or diathermic oil, which is passed through a heat sink 74 outside the chamber 68.

A flange 75 is applied, for example welded, to the mouth of the metal casing 61 and internally delimits an opening 76 for access to the chambers 68 and 67; said flange protrudes externally with respect to the casing and acts as support for two or more pneumatic or hydraulic double-action jacks 77 and 78 which are arranged parallel to the axis X—X of the casing 61; their respective stems 79 and 80 are directed away from the casing 61. The stems 79 and 80 support a door 81 for closing the opening 76; said door has, on the face directed towards the flange 75, an annular sealing gasket 82 which is meant to abut against the flange 75.

The door 81, by virtue of the action of the jacks 77 and 78, which is coordinated in any suitable manner, for example by means of a control unit (not shown in the drawings), can be moved between an open position, as shown in the drawing, and a closed position adjacent to the flange 75.

The door 81 furthermore supports, on the side directed towards the opening 76, one or more part holders, for example a pan 83 on which it is possible to load a dental prosthesis 84 formed by a cast-titanium support and by false teeth made of a ceramic material, which must be fired in the titanium support. More specifically, the pan 83 is fixed at the tip of a stem 85 which is mounted so that it can slide through the door and can be actuated by a double-action jack 86 arranged on the other side of the door and rigidly coupled thereto.

The jack 86 and the stem 85 can be advantageously arranged coaxially to the axis X—X.

The extension of the stem 85 is such that once the door 81 has been moved into its closed position by the jacks 77 and 78 the pan 83, with its load 84, can be moved into two separate positions, namely at the center of the kiln chamber 67 (maximum extension) and inside the cooling chamber.

One or both of the chambers 67 and 68 can be connected to a source of inert gas, such as an argon cylinder 87, by means of an electric valve 88, and has a discharge hole 89 that is connected to a duct 90 which can be closed by an electric valve 91 and directed to an aspiration system (pump) generally designated by the reference numeral 92.

The chambers 67 and 68 are arranged vertically in the illustrated example, but may have any other arrangement, for example a horizontal one.

The operation of the above described apparatus is very simple.

Starting from a condition in which the door 81 is fully open, as shown in the drawing, it is possible to easily access the pan 83 to load the prosthesis 84 on it. Then fluid is supplied to the jacks 77 and 78 so as to make their respective stems 79 and 80 retract and make the door 81 sealingly close the opening 76 by virtue of the gasket 82, which is pressed against the flange 75.

The jack 86 is then energized and extends its stem 85 so as to move the pan 83 and the part 84 to the center of the upper firing region or kiln 67. At this point the aspiration system 92 is activated while the electric valve 88 remains closed, until a vacuum of 4 millibar is produced; the electric valve 88 is then opened to feed argon into the chambers 67 and 68, so as to create an inert atmosphere in them.

The electric valve 88 is closed and power is fed to the electric resistors 69 in order to obtain a firing temperature of for example 800° C. inside the kiln 67. The time for which the prosthesis remains at the firing temperature of course depends on the type of ceramic material being used.

Once firing is complete, power is removed from the resistors 69 and the jack 86 is activated, making its stem retract and thus lowering the pan 83, which moves into the quick cooling region 68 while remaining in an inert atmosphere at all times.

At this point the forced circulation of heat-transferring fluid (diathermic oil) through the cooling system 73, and thus through the coil 72, is activated.

In order to further accelerate the cooling process it is also possible to feed cold argon into the chamber 68, for example by opening the electric valve 88.

Cooling can be total or partial, i.e. below the oxidation temperature of titanium, which is approximately 250° C.; once it has been achieved, the forced circulation of oil through the system 73 is interrupted and the jacks 77 and 78 are activated, moving the door 81 into the open position, where the prosthesis 84 can be easily recovered and a new loading, firing and cooling cycle can begin.

The entire operating cycle of the apparatus can of course be controlled by a program by means of a suitable control unit.

It is evident that the above described apparatus allows to drastically reduce the firing and cooling times in an inert and controlled atmosphere without requiring interventions or transfers or other manual movements of the part to be fired and then cooled.

The apparatus of FIG. 2 is susceptible of numerous modifications and variations.

Thus, for example, instead of the jacks 77 and 78 and/or 86 it is possible to use any other suitable linear actuator.

The door 81 may also be pivoted to the flange 75 or to the casing 61; in this case it is possible to provide a single actuator for opening and closing it.

Furthermore, the kiln section 67 and the cooling chamber section 68 can be separated by a movable insulating partition, for example of the shutter-like type, or of the moving-wall type that can be raised or lowered (by the movable unit formed by the part 81, by the pan 83, and by other suitable devices) inside the kiln section, so as to close said kiln section during the cooling of the part 84.

What is claimed is:

1. Process for casting one or more loads of titanium in an inert atmosphere and under controlled pressure which comprises, in sequence:

preparing a metal load to be cast in a crucible located adjacent to a casting cylinder with refractory and an impression, said crucible and said cylinder being arranged within a sealed casting chamber that can be tilted and has electric-arc heating means for said load, means for aspirating air from the crucible section and from the cylinder section, at least one source for delivering inert gas to the crucible section, and a vent valve;

providing a vacuum of at least 4 millibar within the chamber, said vacuum being controlled by a Pirani device by aspirating from the cylinder section in order to adequately degas the refractory material that delimits the casting impression;

supplying inert gas at a low pressure, of approximately 0.2 bars, to pre-flush the casting chamber;

activating electric-arc means to melt the load;

interrupting the aspiration;

supplying inert gas until the casting chamber is saturated;

tilting the casting chamber to cast from the crucible into the casting cylinder;

supplying inert gas at a relatively high pressure to push the molten metal so that it enters the material inside the casting cylinder;

externally discharging in a controlled manner the inert gas at a threshold value that is equal to, or slightly higher than, the external atmospheric pressure, so as to have casting at constant and moderate pressure;

removing the casting cylinder from the casting chamber.

2. Process according to claim 1, wherein the initial vacuum before melting and casting occur is maintained for at least two minutes so as to produce high degassing of the refractory.

3. Process according to, claim 1, wherein the aspiration means are disconnected after the activation and triggering of the electric arc to melt the load.

4. Process according to claim 1, wherein during the melting of the load the inert gas is injected with a flow-rate of four liter per minute for approximately thirty seconds.

* * * * *